United States Patent [19]
Murphy et al.

[11] Patent Number: 5,616,562
[45] Date of Patent: Apr. 1, 1997

[54] METHODS AND COMPOSITIONS USING SUBSTANCE P TO PROMOTE WOUND HEALING

[76] Inventors: Christopher J. Murphy, 858 Terry Pl., Madison, Wis. 53711; Ted W. Reid, 3511 43rd St., Lubbock, Tex. 79413; Mark J. Mannis, 5061 Keane Dr., Carmichael, Calif. 95608

[21] Appl. No.: 279,991

[22] Filed: Jul. 25, 1994

Related U.S. Application Data

[63] Continuation-in-part of Ser. No. 148,021, Nov. 4, 1993, abandoned, which is a continuation of Ser. No. 13,676, Feb. 4, 1993, abandoned, which is a continuation of Ser. No. 876,805, Apr. 29, 1992, abandoned, which is a continuation of Ser. No. 758,330, Aug. 28, 1991, abandoned, which is a continuation of Ser. No. 515,371, Apr. 27, 1990, abandoned.

[51] Int. Cl.$^6$ ................................................ A61K 38/10
[52] U.S. Cl. ...................... 514/15; 424/78.04; 424/78.06
[58] Field of Search .............................. 514/15; 530/312, 530/327; 424/78.04, 78.06

[56] References Cited

U.S. PATENT DOCUMENTS

| | | | |
|---|---|---|---|
| 3,862,114 | 1/1975 | Scandrett | 514/15 |
| 4,059,693 | 11/1977 | Stewart | 514/15 |
| 4,549,986 | 10/1985 | Evans et al. | 530/324 |
| 4,861,757 | 8/1989 | Antoniades et al. | 514/3 |
| 4,889,919 | 12/1989 | Murray et al. | 530/399 |
| 5,070,075 | 12/1991 | Rotwein et al. | 514/12 |
| 5,093,317 | 3/1992 | Lewis et al. | 514/4 |

OTHER PUBLICATIONS

Stjernschantz et al, "Role of Substance P in . . . Eye" *Naunyn–Schmid. Arch. Pharmacol.* 321:329–335 (1982).

Tomlinson, et al., "Deficient Axonal Transport of Substance P in Streptozocin–Induced Diabetic Rats" (1988), *Diabetes*, 37:488–493.

Gorio, et al., "Peptide Alterations in Autonomic Diabetic Neuropathy Prevented by Acetyl–L–Carnitine" (1992), *Int. J. Clin. Pharm. Res.*, 12:(5–6):225–230.

Robinson, et al., "Axonal transport and tissue contents of substance P in rats with long–term streptozotocin–diabetes. Effects of the aldose reductase inhibitor 'Statil'" (1987), *Statil. Brain Res.*, 426:339–348.

(List continued on next page.)

*Primary Examiner*—Stephen G. Walsh
*Attorney, Agent, or Firm*—Townsend and Townsend and Crew LLP

[57] ABSTRACT

Healing of wounds in mammalian tissue may be enhanced by the application of certain neuropeptides, optionally in combination with known growth promoting hormones. Exemplary neuropeptides include tachykinins, such as substance P, substance K, and the like, as well as calcitonin gene-related peptides. The compositions include a carrier or vehicle suitable for topical application and are utilized by applying to the site of the wound. Wounds resulting from trauma, surgery, and disease may be treated. The compositions promote elaboration of cellular matrices and development of cellular attachment mechanisms in addition to stimulating cellular proliferation.

7 Claims, 13 Drawing Sheets

CORNEAL WOUND HEALING OF GALACTOSEMIC RATS TREATED WITH SUBSTANCE-P

OTHER PUBLICATIONS

Fowler, "Wound Healing in the Corneal Epithelium in Diabetic and Normal Rats" (1980), *Exp. Eye Res.*, 31:167–179.

Yee, et al., "Corneal endothelial changes in diabetic dogs" (1985), *Eye Res.*, 4:759–766.

Wyman, et al., "The dog as a model for ocular manifestations of high concentrations of blood sugars" (1988), *JAVMA*, 193(9):1153–1156.

Jones, et al., "Calcitonin Gene–Related Peptide and Corneal Innervation: A Developmental Study in the Rat" (1991), *J. Comp. Neurol.*, 313:132–150.

Di Giulio, et al., "Acetyl–L–Carnitine Prevents Substance P Loss in the Sciatic Nerve and Lumbar Spinal Cord of Diabetic Animals" (1992), *Int. J. Clin. Pharm. Res.*, 12(5/6):243–246.

Datiles, et al., "Corneal Re–epithelialization in Galactosemic Rats" (1983), *Invest. Ophthalmol. Vis. Sci.*, 24:563–569.

Foulks, et al., "Factors Related to Corneal Epithelial Complications After Closed Vitrectomy in Diabetics" (1979), *Arch. Ophthalmol.*, 97:1076–1078.

Schultz, et al., "Diabetic Keratopathy" (1981), *Tr. Am. Ophth. Soc.*, 79:180–199.

Crosson, et al., "Epithelial Wound Closure in the Rabbit Cornea" (1986), *Invest. Ophthalmol. Vis. Sci.*, 27:464–473.

Engerman et al., "Epithelial and Mesothelial Basement Membranes in Diabetic Patients and Dogs" (1982), *Diabetologia*, 23:521–524.

Tullo, et al., "Corneal Sensitivity and Substance P in Experimental Herpes Simplex Keratitis in Mice" (1983), *Invest. Ophthalmol. Vis. Sci.*, 24:596–598.

Fukushi, et al., "Reepithelialization of Denuded Corneas in Diabetic Rats" (1980), *Exp. Eye Res.*, 31:611–621.

Willars, et al., "Substance P levels in peripheral nerve, skin, atrial myocardium and gastrointestinal tract of rats with long–term diabetes mellitus" (1989), *J. Neurol. Sci.*, 91:153–164.

Keoleian, et al., "Structural and Functional Studies of the Corneal Endothelium in Diabetes Mellitus" (1992), *Am. J. Ophthalmol.*, 113:64–70.

Ziche, et al., "$NK_1$–receptors mediate the proliferative response of human fibroblasts to tachykinins" (1990), *Br. J. Pharm.*, 100:11–14.

Stjernschantz et al, *Invest. Ophthalmol. Vis. Sci.* 20(1):53–60 (1981).

Li et al, *PNAS* 77:4379–4381 (Jul. 1980).

Spevak et al, *Byull, Eksp. Biol. Med.* 107(6):739–743 (1989) abstracted in *Biol. Abst.* 89(1):AB–134 Ref No. 1327 (Jan. 1990).

A.K.C. Li et al., *Proc. Natl. Acad. Sci. USA* 77:4379–4381, Jul. 1980.

Zachary et al. (1987) Develop. Biol. 124:295.

Sakiyama et al. (1984) Develop. Brain Res. 13:275.

Shimizu et al. (1984) Naunyn–Schmiedeberg Arch. Phar. 326:347.

Gamse et al. (1981) Naunyn–Schmiedeberg Arch. Phar. 317:140.

Tervo (1981) Acta Ophthal. 59;737.

Lembeck et al. (1981) Naunyn–Schmiedeberg Arch. Phar. 316:240.

Nilsson et al. (1985) Nature 315:61.

Nilsson et al. (1986) Biochem. Biophys. Res. Comm. 137:167.

Payan (1985) Biochem. Biophys. Res. Comm. 130:104.

Payan et al. (1983) J. Immunol. 131:1613.

Payan et al. (1984) J. Immunol. 133:3260.

Lotz et al. (1987) Science 235:893.

Gamse et al. (1986) Neuroscience Letters 64:287.

Tanaka et al. (1985) J. Cell. Physiol. 123:191.

Quirion and Dam in: *Substance P Metabolism and Biological Actions,* Jordan and Oehme, eds., Taylor & Francis, London, 1985, Chapter 4, "Multiple Tackykinin Receptors", p. 46.

A 5MM CENTRAL CORNEAL EPITHELIAL DEFECT WAS MADE SUBSTANCE-P CONTENT WAS DETERMINED AT THE TIME OF INITIAL WOUNDING, 1 DAY AND 2 DAY POST WOUNDING

METHODS AND COMPOSITIONS USING SUBSTANCE P TO PROMOTE WOUND HEALING

CROSS REFERENCE TO RELATED APPLICATION

This application is a continuation-in-part of application Ser. No. 08/148,021, filed Nov. 4, 1993, now abandoned, which was a continuation of application Ser. No. 08/013, 676, filed Feb. 4, 1993, now abandoned, which was a continuation of application Ser. No. 07/876,805, filed Apr. 29, 1992, now abandoned, which was a continuation of application Ser. No. 07/758,330, filed Aug. 28, 1991, now abandoned, which was a continuation of application Ser. No. 07/515,371, filed Apr. 27, 1990, now abandoned.

BACKGROUND OF THE INVENTION

1. Field of the Invention

The present invention relates generally to methods and compositions for the enhancement of cellular proliferation and the treatment of wounds and other disorders. More specifically, the invention relates to the use of neuropeptides for wound treatment in general and corneal wound treatment in particular.

Traumatic injury and disease can cause damage to the skin, tissue, and body organs which requires cellular regeneration for healing. Accidental injuries such as cuts, abrasions, burns, and intentional surgical procedures result in wounds which can affect large areas of the skin or affected body organs and can require lengthy periods to heal. Long healing times are a particular problem with denervated regions of the extremities and with wounds on sensitive areas, such as corneal wounds, which are difficult to treat over prolonged periods. For these reasons, it would be desirable to provide methods and pharmacological agents which can be used to promote rapid healing of wounds and other injuries to the skin, tissue, and body organs.

A variety of cellular growth promoting hormones have been identified which can enhance cellular proliferation which have been used in wound treatment, including corneal wound treatment. Exemplary growth promoting hormones include epidermal growth factor, transforming growth factor β, insulin-like growth factor, platelet-derived growth factor, and the like. While use of these hormones continues to hold promise, no one growth promoting agent can be optimal for all situations. Thus, it would be desirable to identify additional substances and compositions which have therapeutic value as growth promoting agents, and it would be further desirable to identify substances and compositions which are capable of enhancing or modulating the effect of these and other growth promoting substances.

In addition to cellular proliferation, wound healing requires the elaboration of excellular matrices and development of cellular attachment mechanisms in order to achieve normal tissue morphology. For example, the formation of fibronectin is an important function in normal wound healing. Without sufficient expression of fibronectin and other cellular matrix substances, regenerated tissue can have an abnormal morphology. Thus, it would be desirable to identify substances and compositions which could promote such additional wound healing responses.

For the above reasons, it is an object of the present invention to provide pharmacological agents and formulations useful for the topical treatment of wounds and other disorders. Desirably, the compositions will be capable of providing a potent mitogenic activity which enhances the proliferation of epithelial cells, fibroblasts, and the like. The compositions should also be capable of stimulating the expression of extracellular matrices and development of cellular attachment mechanisms which contribute to normal morphology in the healed tissue. Preferably, the compositions should be capable of enhancing or modulating the growth promoting activity of other growth promotants. The compositions should be suitable for topical application to the skin and body organs, including the eye and should further be suitable for incorporation into a wide variety of delivery vehicles.

2. Description of the Background Art

Substance P

Substance P and substance K have been found to provide enhanced proliferation in cell cultures of smooth muscle cells and human skin fibroblasts (Nilsson et al. (1985) Nature 315: 6; Nilsson et al. (1986) Biochem. Biophys. Res. Comm. 137: 167; and Payan (1985) Biochem. Biophys. Res. Comm. 130: 104). Substance P enhances proliferation of human T-lymphocytes (Payan et al. (1983) J. Immunol. 131: 1613), and such enhancement is mediated by specific receptors for substance P (Payan et al. (1984) J. Immunol. 133: 3260). Substance P has also been found to stimulate the release of prostaglandin $E_2$ ($PGE_2$) from and enhance the proliferation of rheumatoid synoviocytes (Lotz et al. (1987) Science 235: 893). See also, Zachary et al. (1987) Dev. Bio. 124: 295. Substance P has been identified in developing ocular tissue by immunofluorescence (Sakiyama et al. (1984) Brain Research 315: 275). Systemic capsaicin treatment blocks the activity of substance P in animal models and can cause corneal ulcers (Shimizu et al. (1984) Naunyn-Schmiedeberg's Arch Pharmacol. 326: 347; Gamse et al. (1981) Naunyn-Schmied. Arch. Pharm. 317: 140; Tervo (1981) Acta Ophthal. 59: 737; Lembeck et al. (1981) Naunyn-Schmied. Arch. Phar. 316: 240; Gamse et al. (1986) Neuroscience Lett. 64: 287; and Tanaka et al. (1985) J. Cellular Physiol. 123: 191). Substance P and other tachykinins receptors are described in Quirion and Dam in: *Substance P Metabolism and Biological Actions*, Jordan and Oehme, eds., Taylor & Francis, London, 1985, Ch. 4., the disclosure of which is incorporated herein by reference.

Neuropeptides and Diabetes/Galactosemia

Diabetes has adverse effects on many tissues including the cornea. Diabetic patients have been shown to have a very high frequency (approx. 50%) of corneal epithelial abnormalities (Schultz et al. (1982) *TRANS. AM. OPHTHALMOL. SOC.* 79: 180). It has been suggested that the corneal epithelia of diabetic animals has an increased rate of exfoliation (Fowler (1980) EXP. EYE RES. 31: 167–179) and the basement membranes of the eye are thickened in diabetic humans and animals (Engerman and Colquhoun (1982) *DIABETOLOGIA* 23: 521–524). Corneal endothelial morphology is also altered in prolonged diabetic states in man and dogs (Yee et al. (1985) *EYE RES.* 4: 759–766; (Keoleian et al. (1992) *AMERICAN JOURNAL OF OPHTHALMOLOGY* 113: 64–70). During the course of prolonged retinal surgeries to treat proliferative vitreoretinopathy (a commonly encountered vision threatening consequence of long standing diabetes) the corneal epithelium must occasionally be removed to allow better visualization of the posterior segment. Normal patients typically have no difficulties in re-epithelializing the corneal surface while diabetic patients frequently have delayed healing (Foulks et al. (1979) *ARCH.*

OPHTHALMOL 97: 1076–1078). Impaired corneal epithelial wound healing has also been documented in diabetic rats (Fukushi et al. (1980) EXP. EYE RES 31: 611–621) and in galactosemic rats (Datiles et al. (1983) INVEST. OPHTHALMOL VIS. SCI. 24: 563–569).

The effect of diabetes on SP content varies with the structure being investigated. Deficits in anterograde and retrograde transport of SP has been documented in the nerves of diabetic rats (Robinson et al. (1987) STATIL. BRAIN RES. 426: 339–348; Tomlinson et al. (1988) DIABETES 3: 488–493). Significant reduction of SP-like immunoreactivity was shown in the spinal cord (De Giulio et al. (1992) INT. J. CLIN. PHARMACOL. RES. 12 (5–6): 243–6) sciatic nerve (Di Giulio et al. (1992) supra, and autonomic nerves (Gorio et al. (1992) INT. J. CLIN. PHARMACOL. RES. 12 (5–6): 225–30) and many peripheral nerves of diabetic rats (Willars et al. (1989) J. NEUROL. SCI. 91 (1–2): 153–64).

It is possible that a significant consequence of diabetic neuropathy is the depletion of available SP which is subsequently associated with altered epithelial properties and impaired wound healing.

SUMMARY OF THE INVENTION

According to the present invention, neuropeptides, including tachykinins, calcitonin gene-related peptide, and analogs thereof, are applied topically to wounds in mammalian tissue to promote healing. Such neuropeptides have been found to possess cellular growth promoting activity when administered alone to a wound in tissue and have been further found to provide enhanced growth promoting activity when combined with other cellular growth promotants, such as epidermal growth factor, transforming growth factor-β, insulin, insulin-like growth factor, nerve growth factor, and platelet derived growth factor. In addition, the neuropeptides have been found to promote the elaboration of cellular matrices and the development of cellular attachment mechanisms which enhance the regeneration of tissue having a substantially normal morphology.

Compositions according to the present invention include the neuropeptide and/or an analog thereof present in a vehicle suitable for topical application and may optionally include a growth promoting hormone, such as one of the growth promotants listed above. According to the method of the present invention, the compositions are applied in an amount and at a concentration sufficient to promote healing of the wound being treated. Wounds which may be treated include cutaneous wounds, corneal wounds, wounds to the epithelial-lined hollow body organs, and the like. Such wounds may result from trauma, surgical procedures, and disease. The treatment may be particularly effective with problematic epithelial wounds, such as in the denervated regions of the extremities and in the cornea.

The compositions of the present invention also include substance P present in a vehicle suitable for topical application in mammalian tissues, in particular, for ocular or cutaneous application. The substance P compositions of the method of the present invention are applied to a substance P deficient patient in an amount and at a concentration sufficient to promote healing of the wound being treated. The wounds which may be treated by substance P include epithelial and corneal wounds, cutaneous non-healing wounds, or wounds that result from any or more of the following conditions of metaherpetic keratitis, viral infection, galactosemic or diabetic keratopathy, thermal or chemical burns, nerve destruction, corneal epithelial defect and failure to heal post penetrating keratoplasty.

BRIEF DESCRIPTION OF THE DRAWINGS

FIG. 8A is the cornea of the eye which received BSS only. FIG. 8B is the cornea from the same capsaicin-treated rabbit which had received SP in BSS.

DESCRIPTION OF THE PREFERRED EMBODIMENTS

Figure 1:
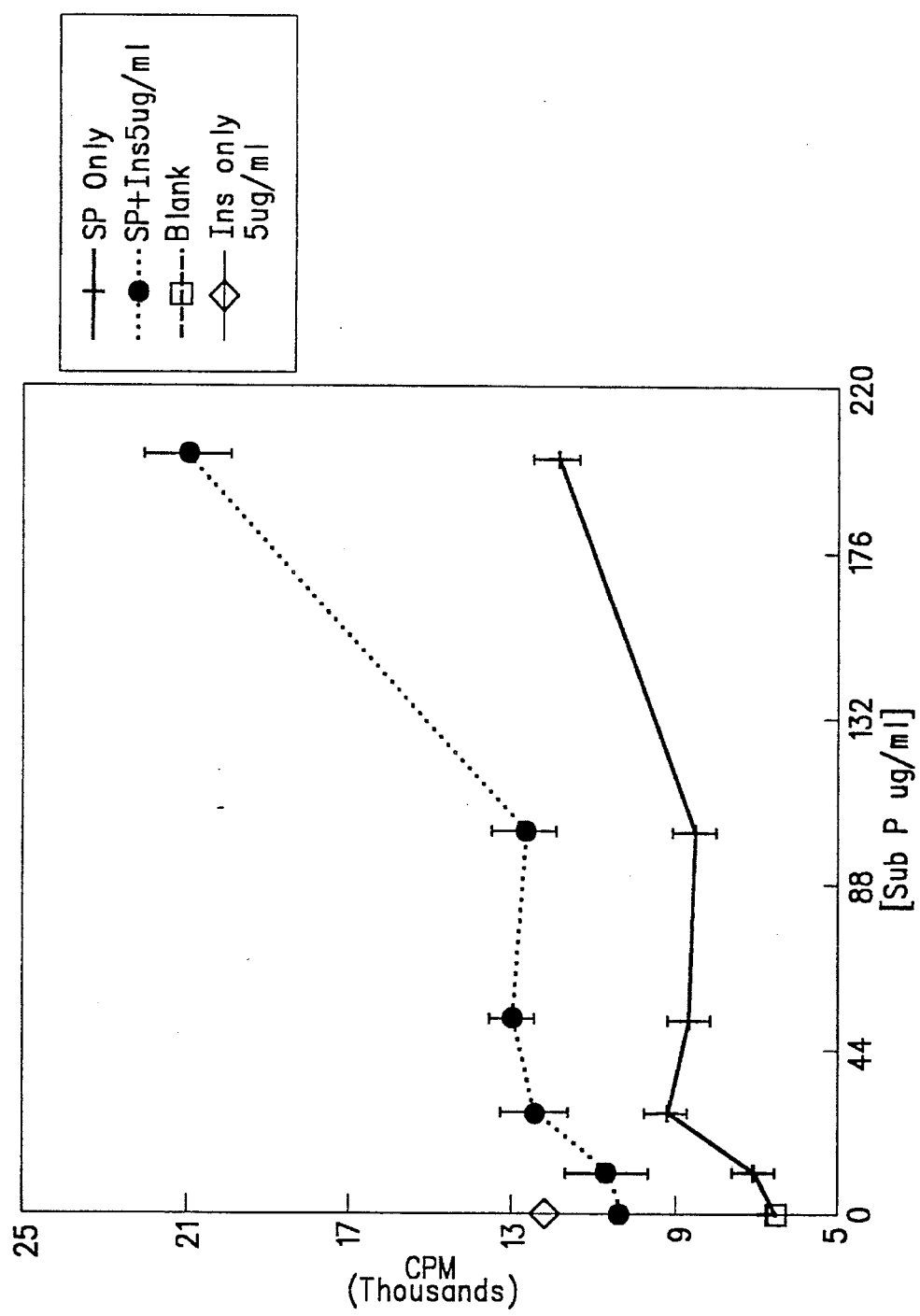
FIG. 1 represents data reported in the Experimental section relating to the dose response effect of substance P on DNA synthesis in corneal epithelial cells in the presence and absence of insulin.

Neuropeptides suitable for use in the present invention include those which possess binding specificity for mammalian cell receptor(s) which are capable of promoting cellular proliferation as well as the elaboration of cellular matrices, such as fibronectin, and the development of cellular attachment mechanisms. Exemplary receptors include the tachykinin receptors as described in Quirion and Dam (1985) supra., the disclosure of which has previously been incorporated herein by reference. Exemplary naturally-occurring neuropeptides include tachykinins such as substance P, substance K (neurokinen A), neurokinen B, physalaemin, eledoisin, and kassinin; calcitonin gene-related peptide; and other sensory nerve neuropeptides; with the use of substance P and its analogs being preferred. For the most part, tachykinins are localized in sensory nerve endings, although not in all cases. Calcitonin gene-related peptide is a sensory nerve neuropeptide, and the present invention may employ sensory nerve neuropeptides in addition to those which are listed above. In addition to naturally-occurring neuropeptides, the compositions of the present invention can utilize synthetic neuropeptides, neuropeptide analogs, neuropeptide fragments, as well as agonists and other substances capable of specifically binding to the neuropeptide receptor(s) of interest.

Substance P is an undecapeptide having the following amino acid sequence:

ArgProLysProGlnGlnPhePheGlyLeuMet NH$_2$

Substance K is a decapeptide having the following formula:

HisLysThrAspSerPheValGlyLeuMet—NH$_2$

Neurokinen B is a decapeptide having the following sequence:

AspMetHisAspPhePheValGlyLeuMet—NH$_2$

Physalaemin is an undecapeptide having the following sequence:

pGluAlaAspProAsnLysPheTyrGlyLeuMet—NH$_2$

Eledoisin is an undecapeptide having the following sequence:

GluProSerLysAspAlaPheIleGlyLeuMet—NH$_2$

Kassinin is a dodecapeptide having the following sequence:

AspValProLysSerAspGlnPheValGlyLeuMet—NH$_2$

Calcitonin gene-related peptide is a 37 amino acid peptide having the following formula:

SerCysAsnThrAlaThrCysValThrHis

ArgLeuAlaGlyLeuLeuSerArgSerGly

GlyValValLysAspAsnPheValProThr

AsnValGlySerGluAlaPhe—NH$_2$

The amino acid sequences of these neuropeptides need not correspond precisely to the above amino acid sequences but rather may include only a portion of such sequences. Usually, the peptides will include at least six of the amino acids, and will preferably include at least nine of the amino acids, and may further include amino acids in addition to those set forth in the above sequences located at either the N-terminus or C-terminus. When additional amino acids are incorporated, the resulting peptide compositions will usually contain 100 or fewer amino acids in total, usually containing fifty or fewer amino acids in total, and more usually containing twenty-five or fewer amino acids in total (in the case of tachykinin derivatives). The neuropeptide compositions of the present invention may also embody substitutions of particular amino acids, although there will usually be no more than one substitution in peptides containing ten or fewer amino acids in total. Such substitutions, of course, should not substantially diminish the desired growth promoting activity of the neuropeptides, and in some cases may in fact enhance the desired activity or may contribute to another desired characteristic, such as longevity (resistance to degradation), persistence, or the like.

A particular fragment of substance P including only amino acids 5–11 (GlnPhePheGlyLeuMet) has been found to be active in promoting cellular growth and may in at least some applications display enhanced activity relative to intact substance P.

A particular substitution peptide where norleucine has been substituted for the C-terminus methionine in substance P has been found to display enhanced activity under at least some treatment conditions, as described in greater detail in the Experimental section hereinafter.

In some cases, it may be desirable to incorporate one of more non-natural amino acids in the synthetic neuropeptides of the present invention. Possible non-natural amino acids will usually have at least an N-terminus and a C-terminus and will have side chains that are either identical to or chemically modified or substituted from a natural amino acid counterpart. An example of a non-natural amino acid is an optical isomer of a naturally-occurring L-amino acid. A particular analog of substance P incorporating non-natural amino acids which has been found to stimulate epithelial cell growth is spantide which has the same sequence as substance P except that a D-Arg is substituted for Arg at position 1, D-Trp is substituted for Phe and Gly at positions 7 and 9, respectively, and Leu is substituted for Met at position 11. Other examples of chemical modifications or substitutions include hydroxylation or fluorination of C—H bonds within natural amino acids.

Such peptide modification techniques are used in the manufacture of drug analogs of biological compounds and are known to one of ordinary skill in the art.

Synthetic peptides having biological and binding activity the same or similar to that of the natural neuropeptides of the present invention may be produced by either of two general approaches. First, the polypeptides may be produced by the well-known Merrifield solid-phase chemical synthesis method wherein amino acids are sequentially added to a growing chain. See, Merrifield (1963) J. Am. Chem. Soc. 85: 2149–2156. Systems for manually synthesizing peptides on polyethylene pegs are available from Cambridge Research Biochemicals, Cambridge, Mass. Automatic peptide synthesis equipment is available from several commercial suppliers, including Applied Biosystems, Inc., Foster City, Calif.; Beckman Instruments, Inc., Waldwick, N.J.; and Biosearch, Inc., San Raphael, Calif. Using such automatic synthesizers according to manufacturer's instructions, peptides may be produced in gram quantities for use in the present invention.

Second, the synthetic neuropeptides of the present invention may be synthesized by recombinant techniques involving the expression in cultured cells of recombinant DNA molecules encoding a gene for a desired portion of a natural or analog defensin molecule. The gene encoding the neuropeptide may itself be natural or synthetic. Conveniently, polynucleotides may be synthesized by well known techniques based on the desired amino acid sequence. For example, short single-stranded DNA fragments may be prepared by the phosphoramidite method described by Beaucage et al. (1981) Tetra. Lett. 22: 1859–1862. A double-stranded fragment may then be obtained either by synthesizing the complementary strand and annealing the strands together under appropriate conditions or by adding the complementary strand using DNA polymerase under appropriate conditions or by adding the complementary strand using DNA polymerase with an appropriate primer sequence. The natural or synthetic DNA fragments coding for the desired neuropeptide may then be incorporated in a suitable DNA construct capable of introduction to and expression in an in vitro cell culture. A particular technique for the recombinant DNA production of substance P is described in Yokota et al. (1989) J. Biol. Chem. 264: 17649, the disclosure of which is incorporated herein by reference.

The methods and compositions of the present invention may also employ synthetic non-peptide compositions that have biological activity functionally comparable to that of the known neuropeptides. By functionally comparable, it is meant that the shape, size, flexibility, and electronic configuration of the non-peptide molecule is such that the biological activity of the molecule is similar to the neuropeptides. In particular, the non-peptide molecules should display comparable mitogenic activity and possess the ability to bind to the particular receptor(s) responsible for the wound healing activity provided by the neuropeptides, preferably including the ability to promote the elaboration of cellular matrices and the development of cellular attachment mechanisms. Such non-peptide molecules will typically be small molecules having a molecular weight in the range from about 100 to 1000 daltons. The use of such small molecules is frequently advantageous in the preparation of pharmacological compositions.

The identification of such nonpeptide analog molecules can be performed using techniques known in the art of drug design. Such techniques include, but are not limited to, self-consistent field (SCF) analysis, configuration interaction (CI) analysis, and normal mode dynamics computer analysis, all of which are well described in the scientific literature. See, e.g., Rein et al., *Computer-Assisted Modeling of Receptor-Ligand Interactions*, Alan Liss, New York, (1989). Preparation of the identified compounds will depend on the desired characteristics of the compounds and will involve standard chemical synthetic techniques. See, Cary et al. *Advanced Organic Chemistry*, part B, Plenum Press, New York (1983).

The compositions of the present invention comprise neuropeptides or their analogs incorporated in a physiologically-acceptable carrier suitable for topical application to the affected area. The compositions may contain from about 0.1 nM to 10 mM neuropeptide, usually containing from about 0.01 µM to 1 mM neuropeptide, and more usually containing from about 0.1 µM to 100 µM neuropeptide. The nature of the carrier will vary depending on the intended area of application. For application to the skin, a cream lotion, or ointment base is usually preferred, with suitable bases including lanolin, Silvadene™ (Marion) (particularly for the treatment of burns) Aquaphor™ (Duke Laboratories, South Norwalk, Conn.), and the like. It will also be possible to incorporate the neuropeptides in natural and synthetic bandages and other wound dressings to provide for continuous exposure of a wound to the neuropeptide. Aerosol applicators may also find use. It is also possible that neuropeptides will be incorporated in or coated on implantable devices, such as heart pacemakers, intralumenal stents, and the like where the growth promoting activity would be of benefit. Coating may be achieved by non-specific adsorption or covalent attachment.

For corneal treatment, the carrier will be suitable for application to the eyes. Preparation of suitable ophthalmic solutions requires careful consideration of factors such as isotonicity, the need for buffering agents, the need for preservatives, and sterilization. Lacrimal fluid is isotonic with blood, having an isotonicity value corresponding to that of an 0.9% sodium chloride solution. Ideally, an ophthalmic solution should have this isotonicity value, but eyes can tolerate isotonicity values as low as that of a 0.6% sodium chloride solution and as high as that of a 2.0% sodium chloride solution without substantial discomfort. Some ophthalmic solutions are necessarily hypertonic in order to enhance absorption and provide a concentration of the active peptide strong enough to exert a prompt and effective action. Suitable ophthalmic carriers include ointments, saline solutions, isotonic saline solutions, such as Sorbi-Care™ (Allergan Pharmaceuticals), Neodecadron™ (Merck, Sharp, and Dhome) and the like. Suitable ointment bases are typified by a product sold under the tradename Lacrilube™.

Other suitable ophthalmic vehicles include boric acid which has a pH slightly below 5.0. Phosphate buffer system may also be employed and adjusted for isotonicity may provide a choice of pH ranging from about 5.9 to 8.0. Pharmaceutical grade of methyl cellulose may also be employed having a variable viscosity.

Figure 2:
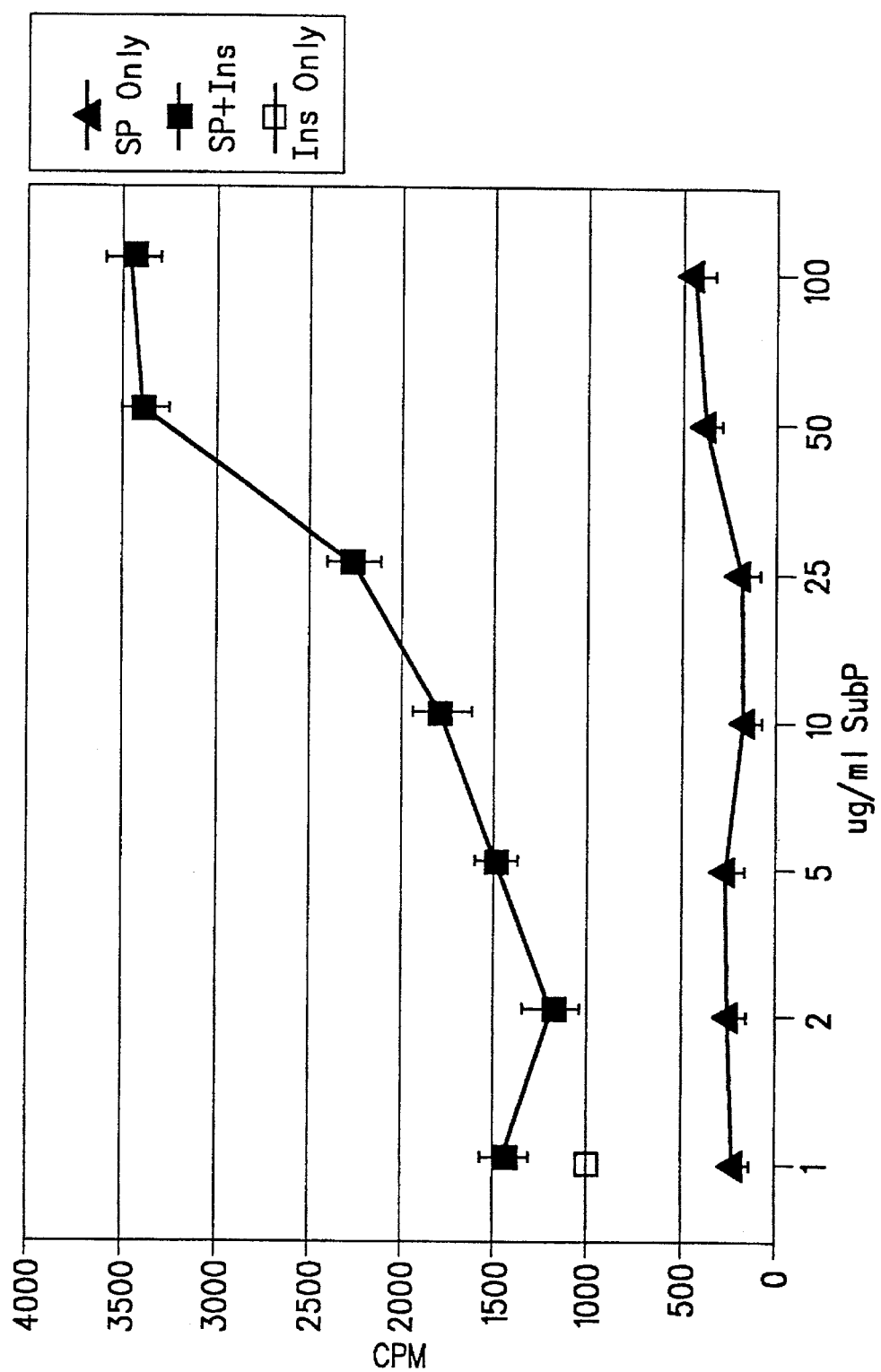
FIG. 2 represents data reported in the Experimental section relating to the dose response effect of substance P on DNA synthesis in lens epithelial cells in the presence and absence of insulin.
Figure 3:
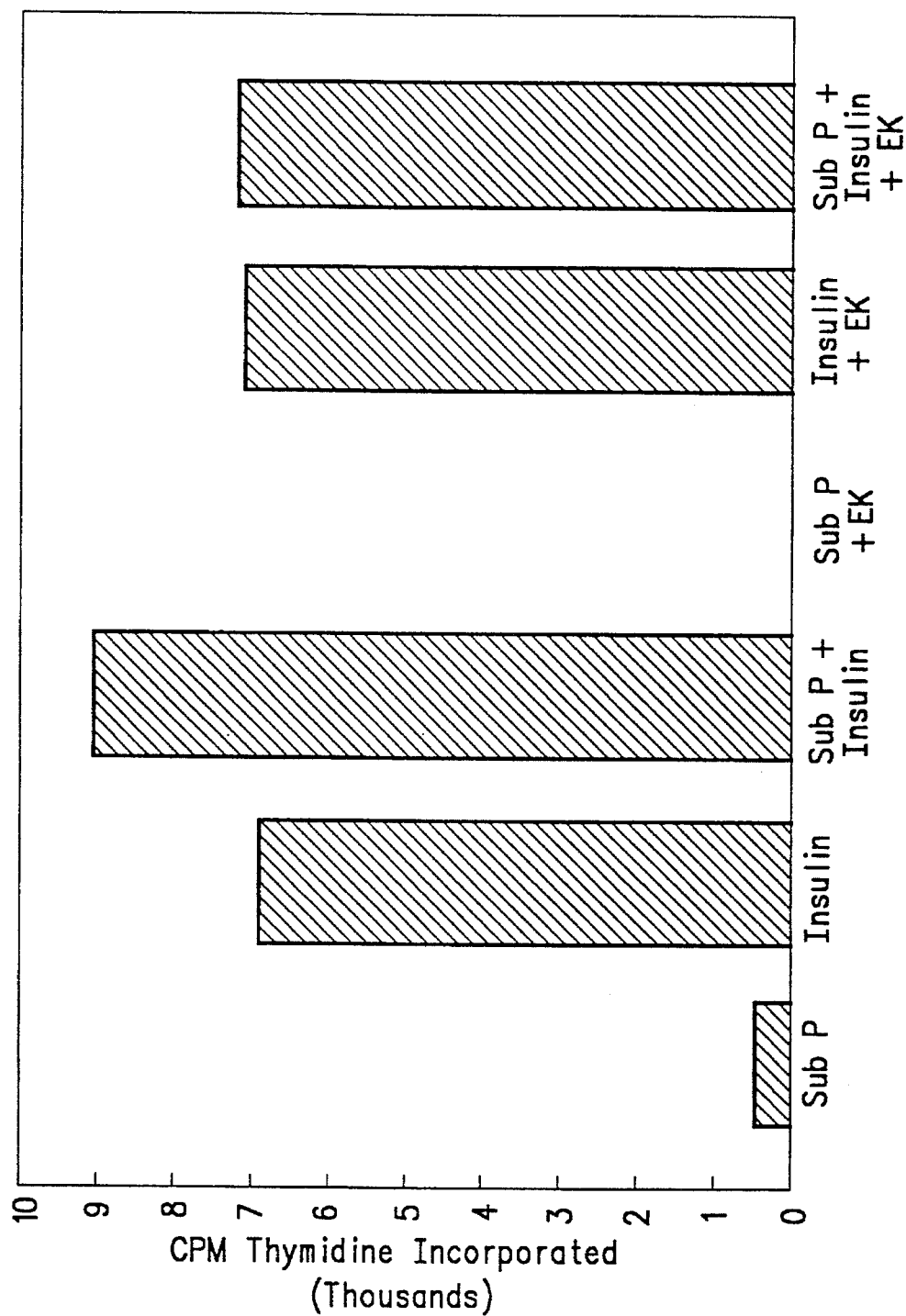
FIG. 3 represents data reported in the Experimental section relating to the effect of enkephalinase on the ability of substance P and insulin to stimulate DNA synthesis.

In addition to neuropeptides, the compositions of the present invention may include other known growth factors, such as epidermal growth factor, platelet-derived growth factor, insulin, insulin-like growth factor, transforming growth factor-$\beta$, nerve cell growth factor, fibroblast growth factor, platelet-derived growth factor and the like. In certain cases, the presence of the neuropeptide may have a beneficial modulating or potentiating effect on the activity of the growth factor as is shown in FIGS. 1–3. The concentrations of the other growth factors will generally be from about 0.1 nM to 10 mM, usually being from about 0.01 µM to 1 mM, and more usually being from about 0.1 µM to 100 µM.

The neuropeptide compositions of the present invention will be useful for treating a wide variety of wounds affecting virtually any tissues of the body. In particular, the compositions will be useful for treating cutaneous wounds affecting the epidermal and dermal layers of the skin, as well as injuries to the cornea and epithelial-lined hollow organs. The wounds may be caused by a wide variety of physical trauma, including cuts, abrasions, thermal and chemical burns, chemical exposure, and the like, as well as from surgical procedures, such as surgical incisions and skin grafting. The wounds may also result from disease including chronic conditions, such as a venous stasis ulcers, diabetic ulcers, including keratopathy, idiopathic corneal epithelial defect and other non-healing (trophic) conditions, such as those which occur in denervated regions of the extremities and post penetrating keratoplasty. Viral infections such as metaherpetic keratitis can also cause the wounds.

The neuropeptide compositions of the present invention will find particular use in treating corneal and scleral wounds, including wounds which affect the epithelial layer, stromal layer and endothelial layers of the eye. Heretofore, eye wounds have required particularly lengthy periods to heal and have been subject to numerous complications.

Substance P and the other neuropeptide compositions of the present invention are particularly suitable for promoting wound healing in patients with substance P deficiency. Especially contemplated is the treatment of cutaneous wounds and non-healing wounds such as occur in diabetes and most especially corneal epithelial wounds in diabetic patients by topical application of compositions containing substance P.

Alteration in SP content may represent an underlying defect in diverse corneal disease processes which result in impaired maintenance and healing of the corneal epithelium and other tissues which normally contain SP. Substance P deficiency can arise as a result of any of the conditions listed above such as physical trauma, viral infection, neuronal degeneration, diseases which affect neural integrity and metabolic diseases such as diabetes. The deficiency can occur as part of a generalized effect or be specific to a tissue or organ site. Substance P deficiency can also induced by treatment with capsaicin which is known to deplete or block the release of SP and effect wound healing (Gallar et al. (1990) *INVEST. OPHTHALMOL. VIS. SCI.* 31: 1968–1974). Systemic or topical treatment with enkephalinase, an enzyme that cleaves SP between amino acid residues 6–7, 7–8, and 9–10, can also deplete substance P. By substance P deficiency is meant a condition whereby the level of substance P within a specific tissue is depleted or lower than the normal level found in the same tissue in a healthy animal or human. Blockage of the synthesis of substance P or of its release to its normal site of function, functional blockade eg. by its antagonist, or the destruction of the substance, either due to disease conditions or artificially induced by treating with drugs and enzymes can all cause or contribute to substance P deficiency. Substance P deficient patients can be humans or mammals, including dogs, cats or horses.

For use in wound treatment, the neuropeptide compositions will usually have a concentration in the range described above. The neuropeptide compositions will usually be applied to the affected area periodically, typically from about 4 to 12 times each day, usually over a period of from about 3 to 14 days, depending on the nature of the wound. In some cases, it may be desirable to apply the compositions indefinitely. The neuropeptide compositions will find particular use in the treatment of wounds resulting from surgery and other intentional interventions where the compositions may be applied immediately after completion of the surgery.

The invention also provides a method for treating wounds in a patient who is substance P deficient. The method comprises applying a neuropeptide selected from the group consisting of tachykinins, calcitonin gene-related peptide, other sensory nerve neuropeptides, and analogs thereof, preferably being substance P or a fragment or analog thereof, to the wound in an amount sufficient to promote healing of the wound.

The following examples are offered by way of illustration, not by way of limitation.

EXPERIMENTAL EXAMPLES

Example 1

Neuropeptide Studies in Vitro

Substance P (SP) was tested for its ability to stimulate cell growth in epithelial cells from both cornea and lens that were arrested in the $G_1/G_o$ phase of the cell cycle in serum free media. SP was found to be weakly stimulatory of DNA synthesis by itself and was strongly stimulatory when combined with insulin. See, FIG. 1 for corneal and FIG. 2 for lens epithelial cells. To test whether this effect was due to SP, 1 µg/ml of enkephalinase (an enzyme that cleaves SP between amino acid residues 6–7, 7–8, and 9–10) was added. As can be seen in FIG. 3, the enzyme destroyed all activity of SP by itself and enhanced activity of SP in the presence of insulin, but did not affect the activity of insulin alone.

In the previous experiment, the enkephalinase was added to the cells at the same time as the SP. When the cells were pretreated with enkephalinase a short period of time (1 to 3 hours) and the enkephalinase then removed, an enhancement of the SP effect was observed, especially in the presence of insulin. It appears that enkephalinase by itself has no harmful effects on the epithelial cells and seems to make them more receptive to the action of SP when it is added.

Several SP analogs were also tested for their ability to stimulate DNA synthesis. An SP analog where norleucine is substituted for methionine at the C-terminus was tested (Nle-SP). Norleucine is a structural analog of methionine where the sulfur is replaced with a $CH_2$ group. It was found that the Nle-SP is more active than SP.

Example 2

Neuropeptide Studies in Vivo
A. Studies Using Rabbits

Figure 4:
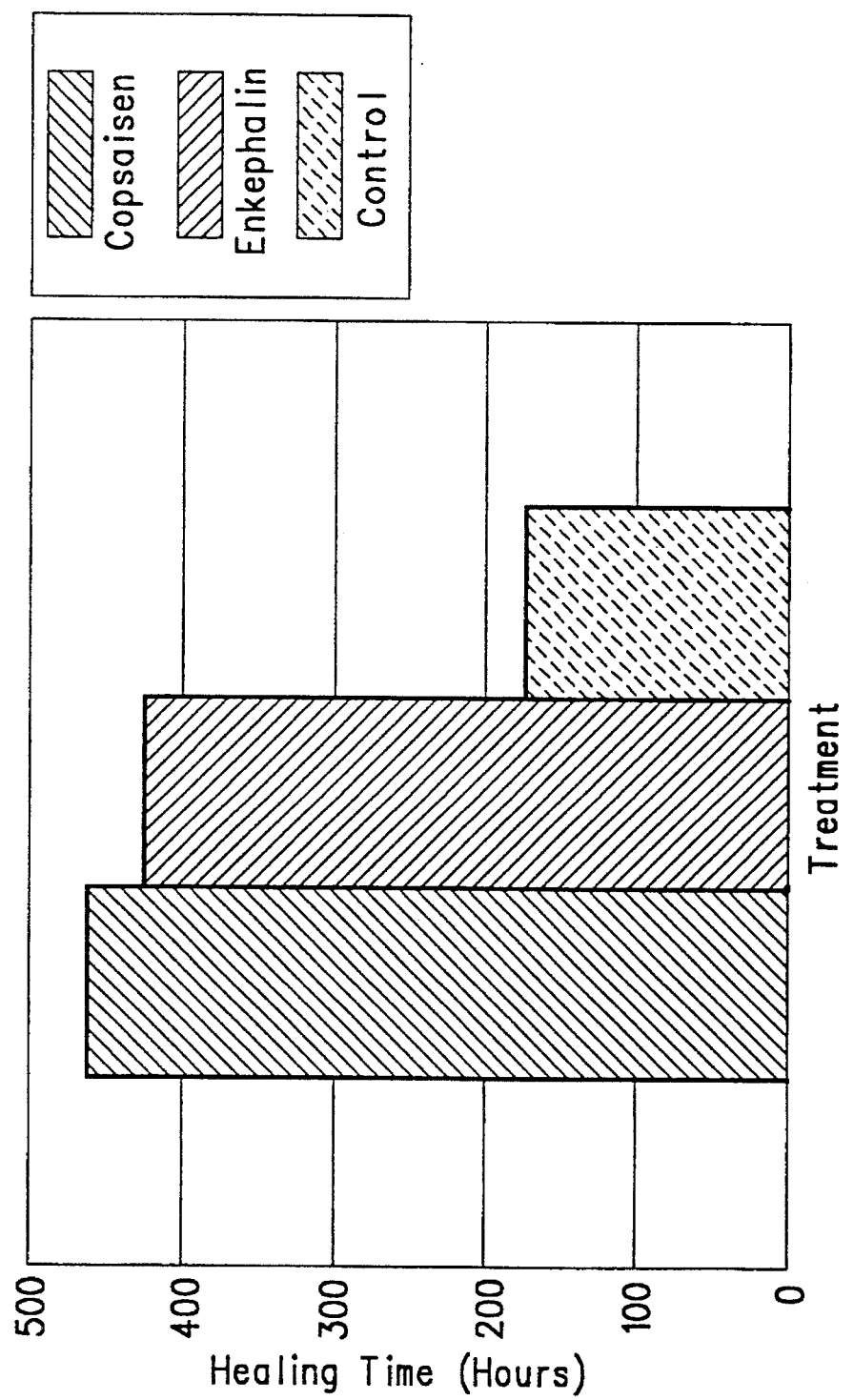
FIG. 4 represents data reported in the Experimental section relating to the healing time necessary for re-epithelialization of corneal wounds in rabbits. Epithelial cells were removed to the limbus. Some rabbits were treated prior to wounding with capsaicin injected subcutaneously. The enkephalinase-treated and control rabbits did not receive capsaicin.

In order to investigate the effect of SP treatment on corneal epithelial cell growth, capsaicin (50 mg/kg) was injected subcutaneously into young rabbits on five consecutive days in order to deplete, lower, or block the release of SP in their corneas. Lidocain was injected subcutaneously into the injection site 10 minutes prior to the capsaicin injection. Three weeks after the last injection, the rabbits were anesthetized (ketamine/rompun), topical anesthetic applied to the cornea and the corneal epithelium of both eyes debrided to the limbal margin of clear cornea. The corneas were stained 2× daily with fluorescein and photographed using a cobalt filter to monitor re-epithelialization. Resultant photographs were projected onto a digitizing board and the surface area of ulceration determined. These data demonstrated that systemic capsaicin dramatically impairs re-epithelization of the cornea when compared to non-capsaicin treated rabbits (460 hours vs 160 hours) as seen in FIG. 4. Clinically, the capsaicin treated rabbits differed from the control rabbits only in their impaired ability to re-epithelialize the denuded stroma. No clinical evidence of impaired lacrimation or other secondary phenomenon that may have impaired wound healing was evident. Additionally, corneal esthesiometry, using a Cochet-Bonnet esthesiometer, yielded similar results in capsaicin and non-capsaicin treated rabbits.

To evaluate the effect of SP depletion using another model, the corneal epithelium was removed from non-capsaicin treated rabbits as described above. Enkephalinase (which breaks down SP) was administered 4× daily to one eye of each bilaterally wounded rabbit. The fellow eye received vehicle only 4× daily. Enkephalinase was found to markedly impair re-epithelialization when compared to the fellow eye treated with vehicle only and that the time course to re-epithelialize the denuded cornea approximated that of rabbits which had been treated with systemic capsaicin (FIG. 4). FIG. 4 underestimates the time course of epithelial healing of both capsaicin treated rabbits and enkephalinase treated corneas for many of these corneas had not re-epithelialized at the termination of the experiments. In 12 rabbits, the enkephalinase treated eye always took longer to heal.

Figure 5:
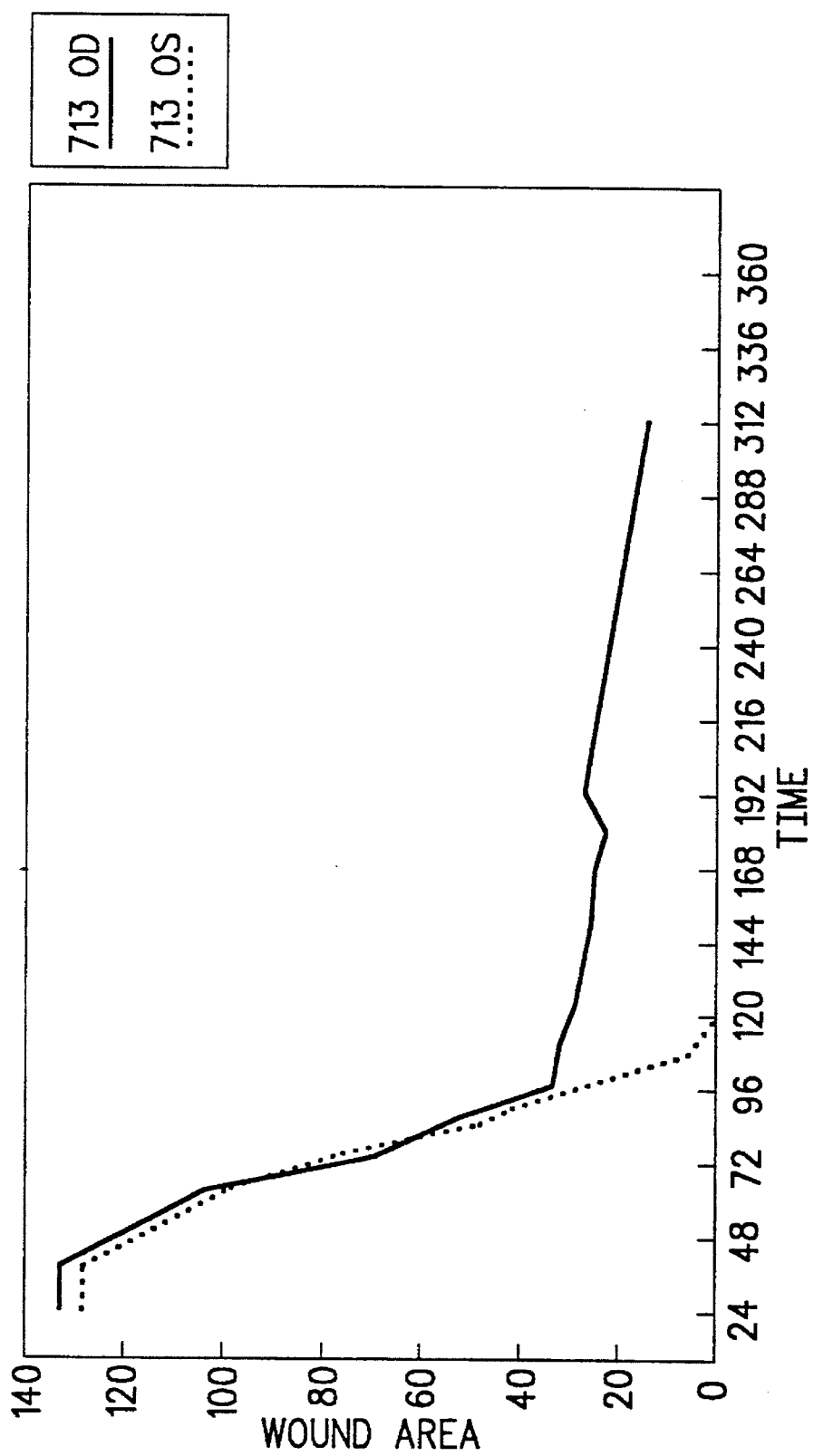
FIG. 5 represents data reported in the Experimental section relating to time required for healing of wounds based on area. The solid line represents the treatment time for enkephalinase-treated eye wounds, while the dotted line represents the treatment time for control eye wounds.

In FIG. 5, typical plots for one rabbit (the other 11 rabbits gave essentially the same results) of wound area with time are presented. The solid line represents the enkephalinase-treated eye while the broken line represents the control without enkephalinase. In each case the enkephalinase treated eye and the vehicle treated eye appeared to heal at the same rate for the first 80 to 90 hours. At this time, the vehicle treated eye would finish healing while the enkephalinase treated eye would slow dramatically in its healing rate. The initial healing rate was probably due to migration of pre-existing cells onto the peripheral wound. After 80 to 90 hours synthesis of new cells is required in order to completely cover the wound. It is also possible that SP may be playing a role in epithelial adherence and the paraxial cells, which are subjected to a relatively greater degree of trauma from desiccation and mechanical forces imparted by lid blinking, are unable to create a secure attachment in the absence of SP.

Figure 6:
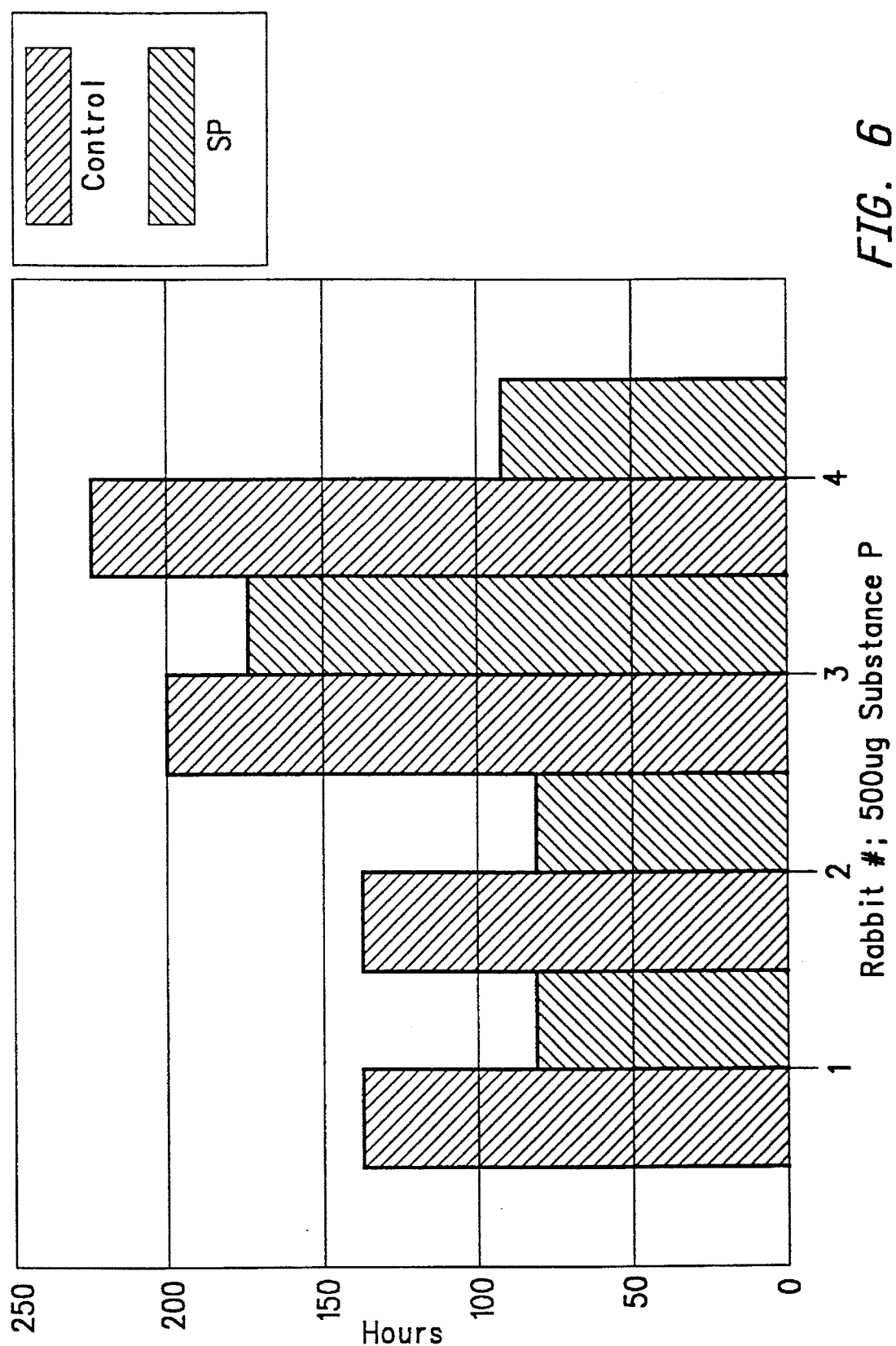
FIG. 6 represents data reported in the Experimental section comparing the healing time for corneal wounds in capsaicin-treated rabbits with and without treatment with substance P (250 μ/ml).
Figure 7:
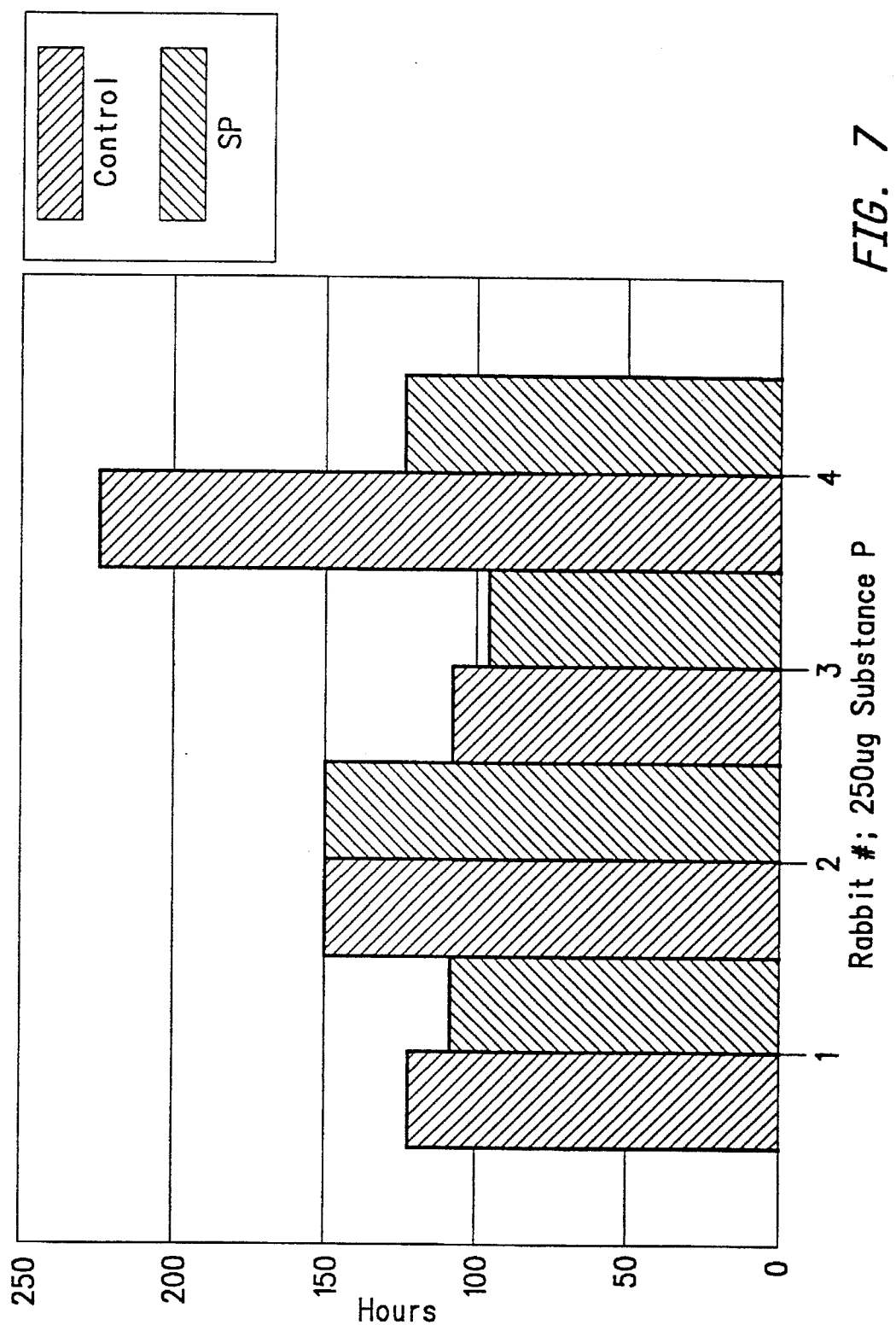
FIG. 7 represents data reported in the Experimental section relating to the healing time for corneal wounds in capsaicin-treated rabbits with and without treatment with substance P (500 μ/ml).
Figure 8B:
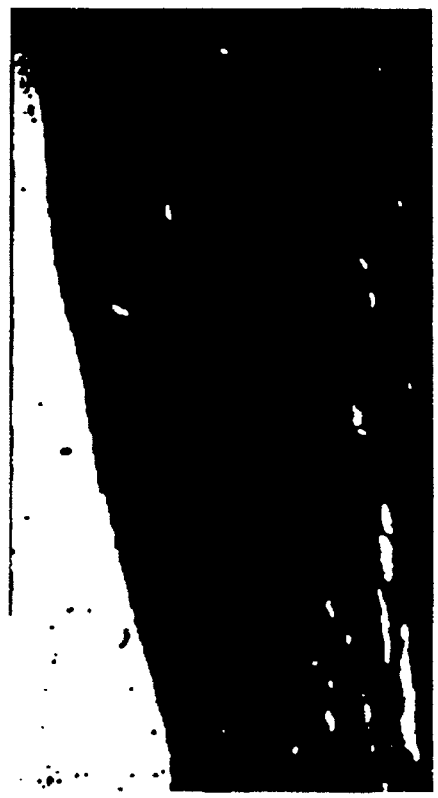
FIGS. 8A and 8B are photomicrographs of the superficial corneas from a rabbit that had received capsaicin prior to wounding.
Figure 8A:

As a further test of the role of SP in the wound healing process, bilateral corneal wounds were formed in capsaicin treated rabbits as described above and SP (either 250 µg/ml or 500 µg/ml) was topically applied to one eye 4× daily while the fellow eye received vehicle only. It was found that treatment with topical SP accelerated the healing process and that this effect was more dramatic when the higher concentration (500 µ/ml) of SP was used (FIGS. 6 and 7).

For both capsaicin-treated rabbits and those treated with topical enkephalinase, regenerated epithelial layers could be easily rubbed off as a sheet of cells after healing of the cornea. This was not found in the control rabbits. Specimens from the various treatment groups were masked and morphologically examined to determine the nature of epithelial adherence. Those morphological findings revealed that the corneal epithelium was poorly adhered in capsaicin-treated rabbits and in normal rabbits which had been treated with topical enkephalinase. Thus, it appears that SP and other neuropeptides contribute to the attachment of epithelial cells during wound healing. Such contribution may take the form of elaboration of extracellular matrices (e.g., fibronectin) as well as development of cellular attachment mechanism, which activity would be in addition to their mitogenic activity in promoting cellular proliferation.

B. Studies Using Dogs

SP content has been shown to be lowered to approximately 30% of control values in corneas of mice that have been infected with herpes simplex virus (Tullo et al. (1983) *INVEST. OPHTH. VIS. SCI.* 24: 596–598). No other studies could be located which specifically investigate SP content in corneal disease states. Here we present data that support that SP content is modulated in canine patients that have chronic, non-septic corneal epithelial defects.

Dogs represent a potentially important model for the study of corneal epithelial wound healing disorders for the following reasons. The clinical features of persistent corneal epithelial defects are very similar between dogs and humans. Background information and preliminary data suggests that many of the clinical features of this condition could be explained by a lowering of SP content. The canine model offers a unique opportunity to study spontaneous disease that closely mimics the human condition. Dogs are the most commonly seen patient in veterinary practice to develop chronic corneal epithelial defects. Thus, tear and cell samples can be obtained for investigation from spontaneously occurring cases. In addition, several large veterinary ophthalmology practices treat chronic epithelial defects by performing superficial keratectomies which would provide the opportunity to examine morphologic specimens from spontaneously occurring cases that closely resemble the disease in man.

Dogs are a well delineated model of the ocular consequences of diabetes. Similar to man, ocular manifestations identified in diabetic dogs include morphologic alterations in the corneal endothelium (Yee et al. (1985) *EYE RES.* 4: 759–766), rapidly developing cataracts (reviewed by Wyman et al. (1988) *JAVMA* 193: 1153–1156), and the development of diabetic retinopathy (Engerman (1976) *DIABETOLOGIA* 23: 521–524).

Corneal Epithelial Wound Healing in the Dog

Preliminary studies show that the process and rate of wound healing is similar to other mammalian species. Two, adult, mixed-breed dogs were anesthetized and unilateral 10 mm central corneal epithelial defects were made by mechanical debridement. The dogs received the analgesic oxymorphone intramuscularly twice daily for 3 days post operatively. One drop of topical BSS was applied to the cornea four times daily. Epithelial wound size was determined twice daily by the topical application of fluorescein and illumination of the cornea with a cobalt light source. The cornea was imaged with a B&W video camera attached to a Macintosh® based image analysis station that employed NIH Image software. A scale was included in all captured images. Actual wound size, correcting for corneal curvature, was calculated as outlined by Crosson et al. (1986) *INVEST. OPHTHALMOL. VIS. SCI.* 27: 464–473). The calculated rate of epithelialization was approximately 50 µm per hour.

SP Content in Animal Models

Figure 9:
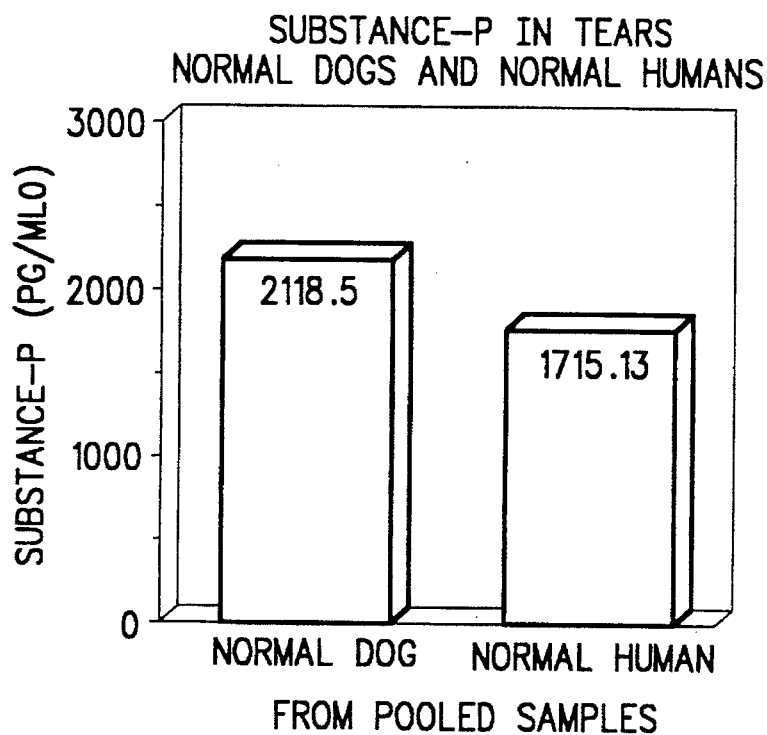
FIG. 9 represents data comparing the amount of substance P in tears of normal dogs and normal humans.
Figure 10:
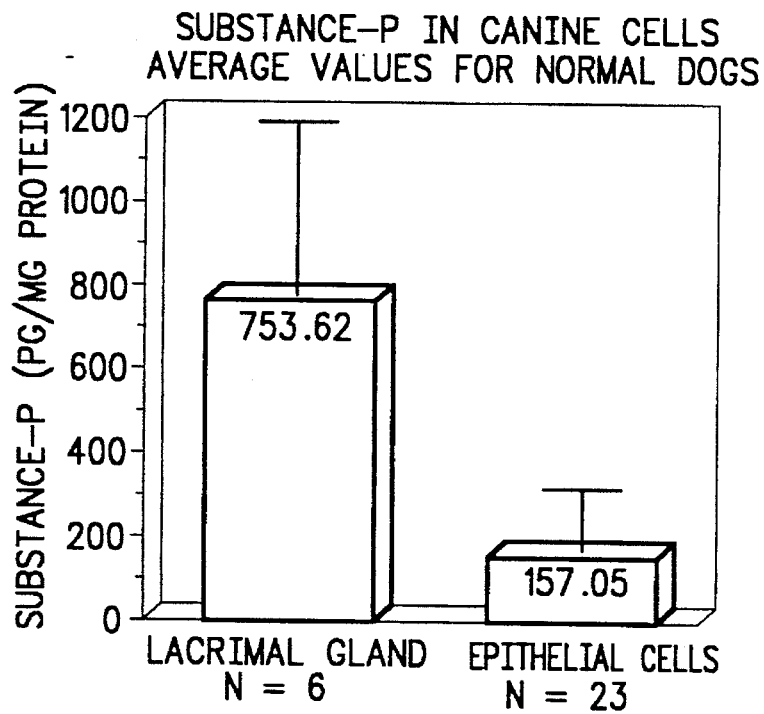
FIG. 10 represents data comparing the amount of substance P in canine lacrimal versus epithelial cells.
Figure 11:
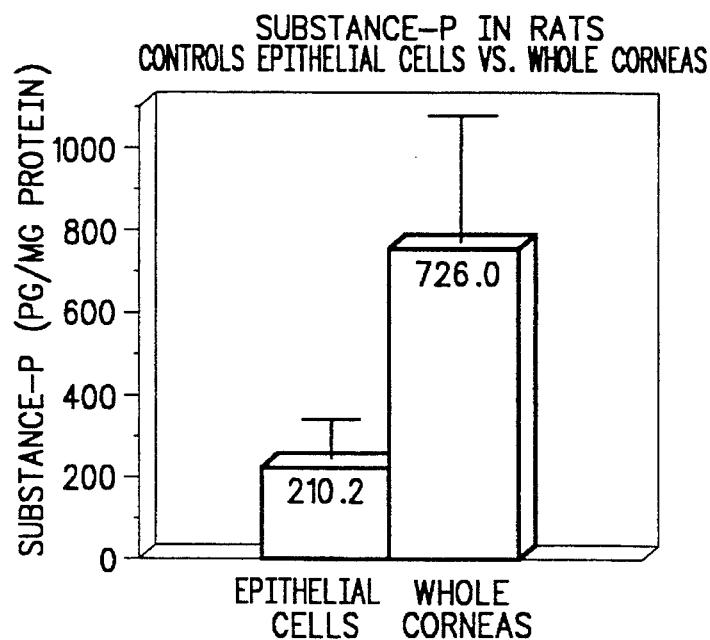
FIG. 11 represents data comparing the amount of substance P in epithelial cells and whole corneas of rats.
Figure 12:
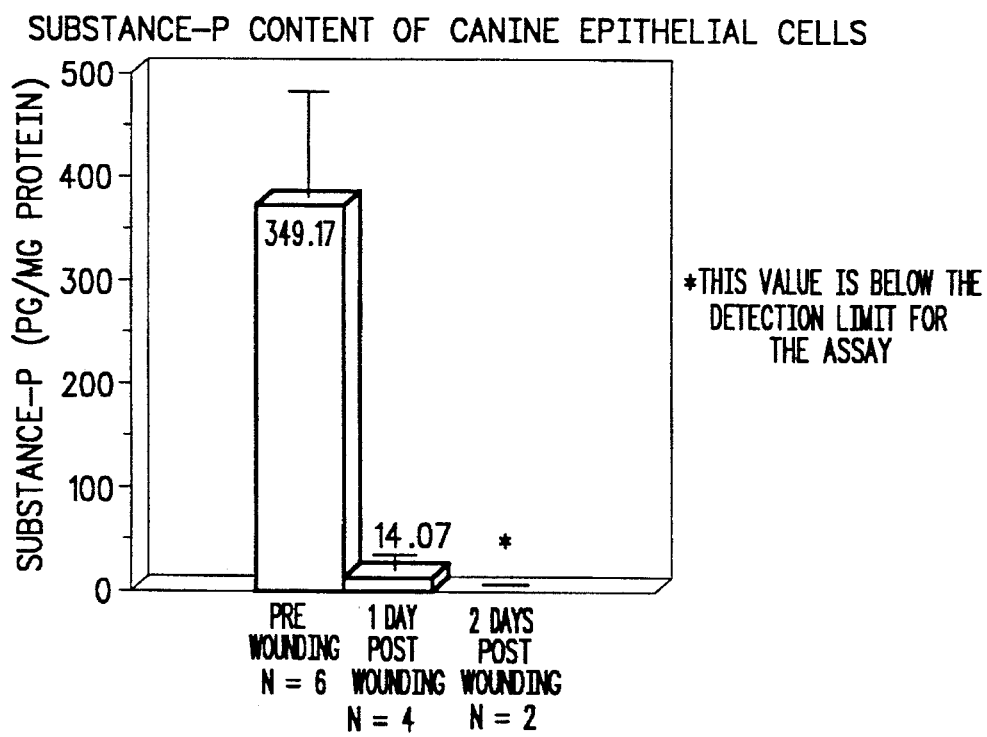
FIG. 12 represents data showing substance P content in corneal epithelial cells during epithelial wounding.

SP was determined to be present in the tears of dogs and humans, the lacrimal tissue of dogs and in the cornea of dogs and rats, as quantitatively measured by RIA (FIGS. 9–11). Additionally, SP immunoreactivity has been documented in the nerves supplying the canine cornea and lacrimal tissue. These findings indicate that SP may be made available to the corneal epithelium not only by its intrinsic nerve supply but also by SP produced in the lacrimal gland and supplied to the epithelium by the tear film. The present data also document canine corneal epithelial SP content to be markedly diminished immediately after the creation of a corneal epithelial defect (FIG. 12).

Sample Collection for RIA

Preliminary studies documented SP to be completely bound to glass microcapillary pipettes necessitating tear collection using small diameter sterile silicone tubing which had been attached to a 25 ga needle on a 1 ml syringe. Preliminary studies had also shown measured SP content to be quite labile if proteolytic enzyme activity was not inhibited. To minimize enzymatic degradation, tears were collected into chilled microcentrifuge tubes until at least 10 µl had been collected, at which time an equal volume of chilled 0.2N perchloric acid was added. Tear SP content was expressed in pg/ml tears.

After irrigation of the globe with saline, corneal epithelial cells were collected by mechanical debridement and placed into 50 µl of chilled distilled $H_2O$, the cells were then ruptured by sonication for 2 seconds. Two µl were then removed for protein determination using the Bradford reagent and an ELISA plate reader. Forty-five µl of chilled 0.2N perchloric acid were then added to the tube to abolish enzymatic activity. These samples were then measured for SP content by radioimmunoassay. SP values are expressed as "pg SP per mg protein." It was found in preliminary experiments that tissue wet wt. was unreliable for comparison for it was affected by such factors as relative humidity of the room and the length of time from anesthetic induction to surgical debridement of the cells.

Whole corneas were dissected free of the globe at the limbus. Lacrimal tissue was meticulously removed from the canine orbit, and then repeatedly diced using 2 razors for 45 seconds. The diced tissue was then placed in 60 µl of distilled water and sonicated (Fisher® dismembrator) at setting 35 for three bursts of 5 seconds. A 4 µl aliquot was then removed for protein determination and 54 µl of 0.2N perchloric acid was added to the remaining sample. The sample was then centrifuged at 7,000 RPM for 15 seconds and the supernatant assayed for SP content. Values of SP are expressed in pg SP per mg protein.

RIA

SP was measured using a double antibody radioimmunoassay using a polyclonal antibody produced against the intact molecule of SP supplied by Dr. Kazlowsky at the University of Texas, Southwestern. The specific methods employed have been reported (Yees et al. (1985); Keoleian et al. (1992) EYE RES. 4: 759–766). This assay has been validated by spike and recovery determinations for each specimen type (tears, cornea, lacrimal tissue) for each species across the entire standard curve. The sensitivity of this assay was approximately 0.2 pg/ml tears. Typical between assay coefficient of variation is~12% at the standard curve midpoint. Typical within assay variation is~7% at the standard curve midpoint.

Immunohistochemistry

Lacrimal and corneal tissues were collected from 4 deeply anesthetized dogs immediately prior to euthanasia; and immersion-fixed whole in ice cold, 4% paraformaldehyde-0.2% picric acid in 0.1M phosphate buffer, (pH 7.3), containing 30% sucrose. Prior to sectioning, 4–6 radial slits were made in the peripheral cornea. All specimens were placed in room temperature, optimal cutting, embedding media. The tissues were then cut in a cryostat at 28 μm and collected in serial order in tissue culture wells filled with ice cold 0.1M PBS. Histochemical demonstration of SP and CGRP was performed on free-floating specimens using a Vectastain ABC Elite kit (Vector Laboratories, Burlingame, Calif.) as reported in the literature (Jones and Marfurt (1991) J. COMP. NEUROL. 313: 132–150). Primary anti-CGRP and anti-SP antibodies were purchased from Amersham (Arlington Heights, Ill.).

Corneal Epithelial Substance P Content During Wounding

Three dogs were placed under general anesthesia and bilateral, 5 mm, central epithelial defects were made by mechanical debridement. Dogs received the analgesic oxymorphone intramuscularly twice daily for 3 days after wounding. The SP content of the collected cells was determined as described in the RIA section above. At 24 hours after wounding, two dogs were anesthetized and 10 mm trephine was used to delineate a central region of both corneas from which the epithelial cells were mechanically debrided and assayed for SP content. The remaining dog had cells removed in an identical fashion 48 hours after wounding.

As can be seen from the results shown in FIG. 12, epithelial wounding brings about a marked reduction in corneal epithelial SP content in migrating cells and in cells peripheral to the wound area.

SP Content in Dogs with Chronic Epithelial Defects

The present studies have documented tear SP content to be significantly lower in canine patients with this spontaneously occurring, non-septic, chronic, corneal healing disorder.

This is a commonly encountered corneal disease of dogs. Similar to chronic, non-healing epithelial defects in man, the lesion is characterized by the presence of an "epithelial lip"—a rim of epithelial cells that extend over the stroma but fail to adhere properly. These defects are typically non or poorly vascularized despite their long standing nature. Dogs were included in this study only after a complete ophthalmic examination (including slit lamp examination) failed to discover an underlying cause for the defect and the defect had to be present for at least 4 weeks. Tears from both eyes of dogs with chronic unilateral corneal epithelial defects were collected and SP content determined by RIA as outlined above. Schirmer tear tests were performed bilaterally (the affected eye had a slightly elevated value) and corneal sensation was evaluated by Cochet-Bonnet esthesiometry which uses a standard nylon filament (the shorter the filament has to be to elicit a blink response the less sensitive the cornea is). Corneal sensation was normal in both eyes of all three patients.

Figure 13:
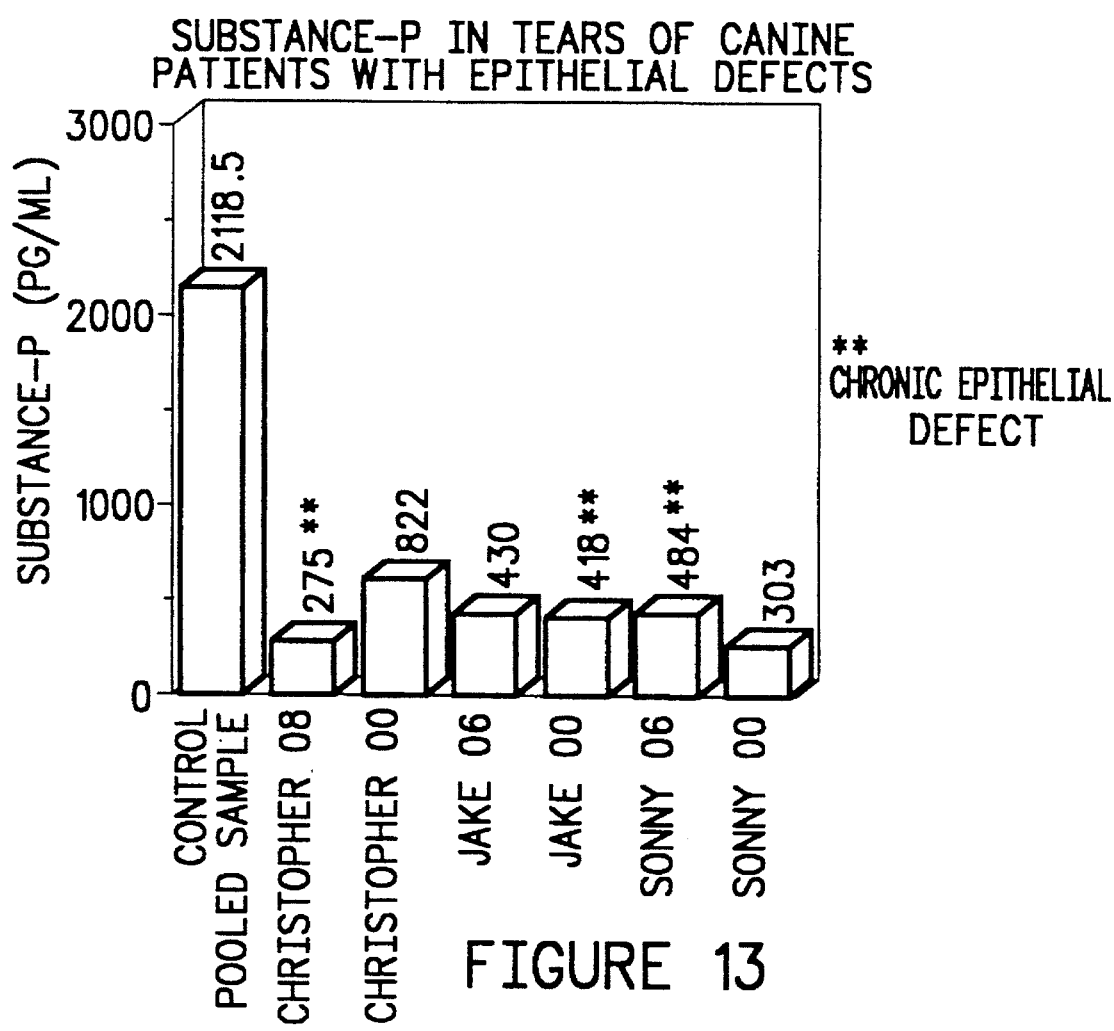
FIG. 13 represents data showing substance P content in tears of canine patients with chronic epithelial defects.

Tear SP content was found to be reduced bilaterally in dogs that have persistent epithelial defects (FIG. 13).

Of extreme interest is the finding that the concentration of SP in the tear film of both eyes is markedly reduced in the 3 patients measured. This speaks against the SP content being lowered by a mere dilutional effect of increased lacrimation. It also needs to be noted that in dogs that present with a persistent epithelial defect the fellow eye is clinically always considered to be a risk for developing a defect. Additionally, it is typical for dogs with this condition to present with multiple recurrent episodes of epithelial defects.

Effect of SP on Wound Healing in Dogs with Persistent Non-Septic corneal Epithelial Defects The present clinical trial suggests topical SP to be an effective therapy in the treatment of persistent non-septic corneal epithelial defects since it accelerated wound healing in these dogs. Nine of ten canine patients with this chronic (up to 4 months) spontaneous corneal epithelial defect completely healed with the topical application of SP.

This was a non-controlled open-label clinical trial conducted on canine patients seen in a specialty referral service for chronic, non-septic corneal epithelial defects. Criteria for inclusion included:

1. Absence of an identifiable underlying cause of the epithelial defect (lid abnormalities, decreased tear production etc.) on complete ophthalmic examination.
2. Persistence of the defect for at least 3 weeks.
3. Unresponsive to traditional therapy (topical broad spectrum antibiotics, some cases had received topical hyper-osmotic therapy, and 5 dogs had not healed after placement of a therapeutic soft contact bandage lens).

After obtaining informed consent from the owners, the dogs were taken into the hospital, an Elizabethan collar was placed (to keep the dog from rubbing its eye) and two drops of 500 μ/ml SP were instilled into the affected eye. The dogs were closely observed for any irritant effect of the drops. The dogs were then treated with one drop 8 times daily for duration of the trial.

Figure 14:
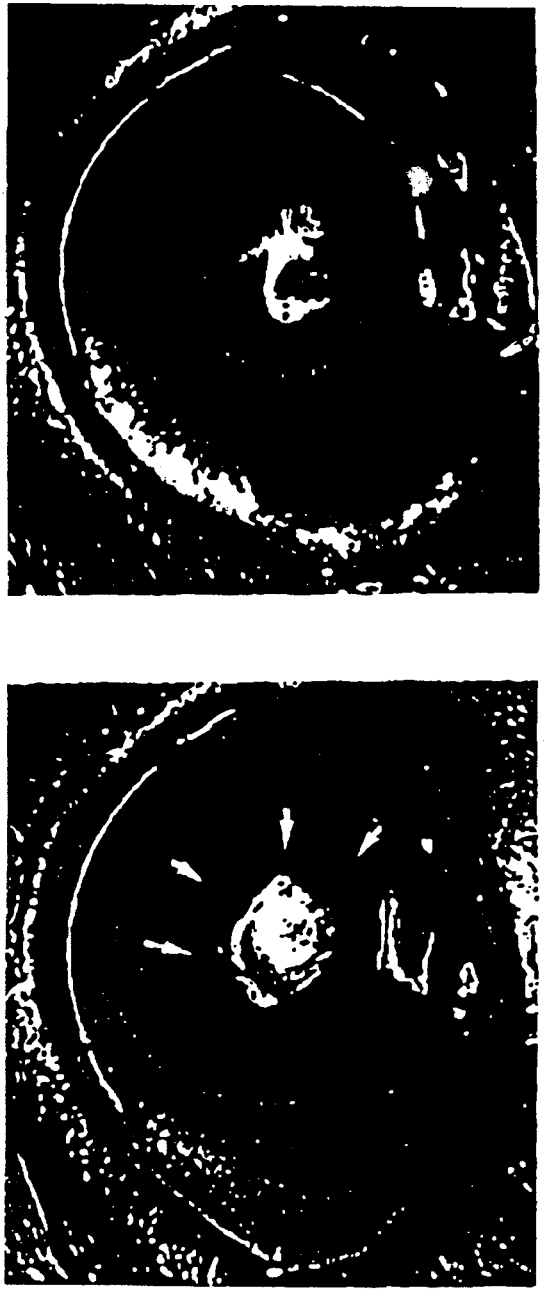
FIG. 14 shows the effect of topical substance P in the treatment of a persistent corneal epithelial defect.
Figure 14:

Topical SP brought about a resolution of the epithelial defects within 2 weeks in 9 out of 10 dogs. The owners generally noted an increased comfort level for their animal within 24 hours of the initiation of therapy. No complications were observed. FIG. 14 shows the effect of topical SP in the treatment of a persistent corneal epithelial defect in a 10 year old male castrated golden retriever that had a persistent epithelial defect for 60 days. It had not healed with topical treatment with triple antibiotic solution and placement of a therapeutic soft contact lens. Corneal sensation was normal. Topical treatment with SP brought about a complete resolution within 2 weeks. Top Left of FIG. 14 shows that at initial visit, the corneal defect is poorly vascularized. After fluorescein staining it can be seen to have a "epithelial lip" at its periphery (arrows). The "epithelial lip" represents an extension of epithelial cells that fail to adhere to the underlying stroma. Top Right: After one week of treatment with topical SP, the epithelial defect was healed and vessels can be seen investing the region. Bottom: After two weeks of treatment the vessels have receded, leading only a faint anterior stromal haze. The epithelium has completely covered the defect.

Taken together, these preliminary data from canine patients are strongly suggestive of SP playing an important role in the development of chronic epithelial defects. In several of the cases healing was brought about in conjunction with vascularization. It is known that SP is mitogenic for vascular endothelial cells (Ziche et al. (1990) *J. PHARM.* 100: 11–14).

Example 3

Effect of SP on Wound Healing in Diabetic and Galactosemic Animals

Galactosemic rats are used as an animal model for diabetes.

In this example, data are presented that show that whole corneal SP was reduced in galactosemic rats and the decreased availability of SP was shown to impair corneal epithelial wound healing in diabetic and galactosemic animals.

Figure 15:
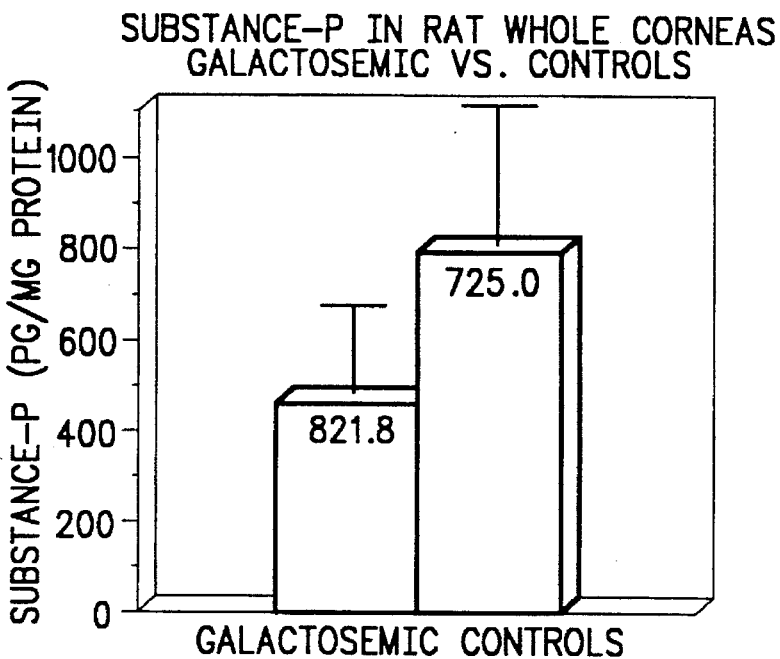
FIG. 15 represents data showing the substance P content in corneas of galactosemic rats.

Young rats were fed a diet containing 50% galactose for 3 weeks (for methods see Datiles et al. (1983) *INVEST. OPHTHALMOL VIS. SCI* 24: 563–569). By this time, all animals had developed galactosemic cataracts. Ten control rats and 8 galactosemic rats were euthanized and whole corneal SP content measured by RIA as outlined above. It was found that the whole corneas of galactosemic rats have lowered SP content compared to controls (FIG. 15).

Preliminary results document impaired wound healing in galactosemic rats compared to controls. The application of topical SP was found to significantly accelerate corneal epithelial wound healing in galactosemic rats.

Eight control rats and 8 galactosemic rats were anesthetized and the corneal epithelium removed to the limbus bilaterally. The analgesic buprenorphine was administered IM twice daily. Eyes were treated topically four times daily. Control rats had BSS applied to both eyes and galactosemic rats received BSS in one eye and 25 µ/ml of SP in BSS in the other. The assignation of which eye received SP was determined in a random fashion and the identity of the drop (i.e. BSS alone or BSS containing SP) was masked from the observers. Fluorescein was applied to the cornea at 24, 36, and 48 hours after wounding and the epithelial defect imaged using a B&W video camera and a high-8 video deck. A mm scale was placed below the eye at each imaging session. Video images were captured into a Macintosh based image analysis station and analyzed using NIH image software. At the completion of data analysis the code was broken (as to which eyes received SP).

Figure 16:
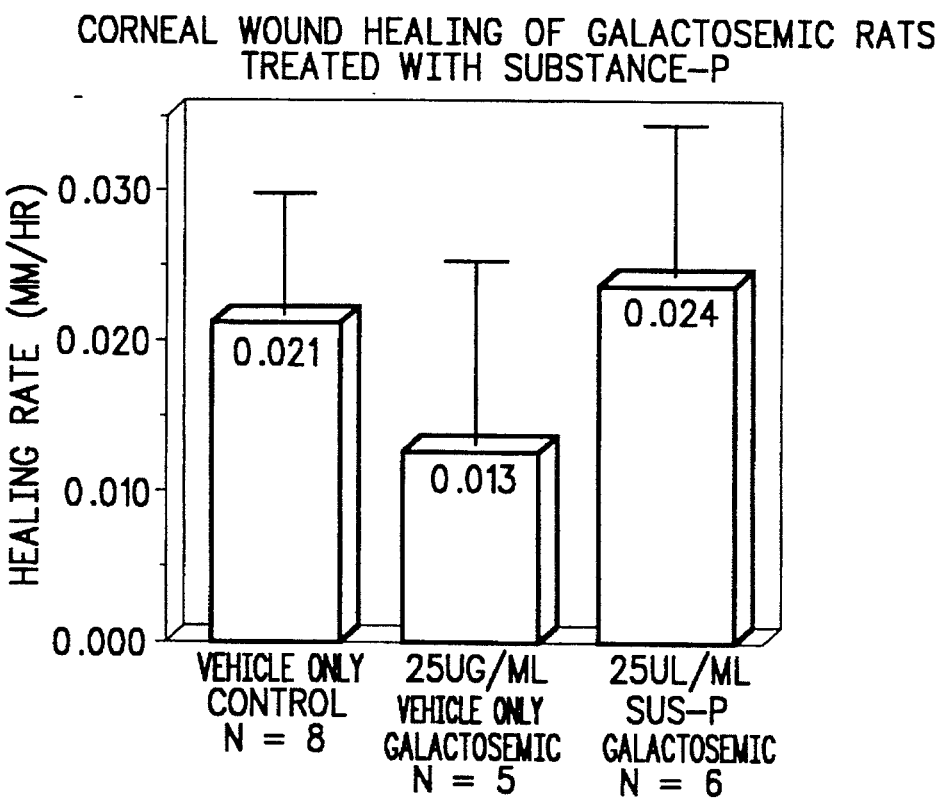
FIG. 16 represents data comparing wound healing in galactosemic rats treated topically with vehicle or substance P.

Impaired epithelial wound healing of galactosemic rats was confirmed and the application of topical SP was found to significantly ($p<0.05$) accelerate corneal epithelial wound healing in galactosemic rats (FIG. 16).

These findings support the hypothesis that diabetic and galactosemic animals have impaired SP expression in the cornea which may contribute to the impaired reparative processes.

Although the foregoing invention has been described in detail for purposes of clarity of understanding, it will be obvious that certain modifications may be practiced within the scope of the appended claims.

What is claimed is:

1. A method for promoting healing of a corneal or an epithelial wound in a substance P deficient patient, said method comprising applying substance P to the wound in an amount sufficient to promote healing of the wound.

2. A method as in claim 1, wherein substance P is applied to a corneal wound.

3. A method as in claim 1, wherein substance P is applied in a physiologically-acceptable carrier at a concentration of at least about 1 µM.

4. A method of claim 1, wherein the substance P deficiency is a result of a condition selected from the group consisting of metaherpetic keratitis, viral infection, galactosemic or diabetic keratopathy, thermal or chemical burns, nerve destruction, corneal epithelial defect and failure to heal post penetrating keratoplasty.

5. A method as in claim 1, wherein the substance P is topically applied to an affected eye.

6. A method as in claim 4, wherein the deficiency is a result of galactosemic or diabetic keratopathy.

7. A composition comprising substance P present in a lotion, cream, or ointment suitable for cutaneous application.

* * * * *